United States Patent
Pyayt

(10) Patent No.: US 9,297,816 B1
(45) Date of Patent: Mar. 29, 2016

(54) DEVICES AND METHODS FOR MEASURING BLOOD COAGULATION

(71) Applicant: Anna Pyayt, Tampa, FL (US)

(72) Inventor: Anna Pyayt, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/134,649

(22) Filed: Dec. 19, 2013

Related U.S. Application Data

(60) Provisional application No. 61/740,639, filed on Dec. 21, 2012.

(51) Int. Cl.
*G01N 33/86* (2006.01)
*G01N 33/49* (2006.01)

(52) U.S. Cl.
CPC ............. *G01N 33/86* (2013.01); *G01N 33/491* (2013.01); *G01N 33/4905* (2013.01)

(58) Field of Classification Search
CPC .................................. G01N 33/86; C12Q 1/56
USPC ............................................... 435/13; 436/69
See application file for complete search history.

(56) References Cited

U.S. PATENT DOCUMENTS

| | | | |
|---|---|---|---|
| 5,986,754 A | 11/1999 | Harding | |
| 6,200,532 B1 * | 3/2001 | Wu et al. | 422/73 |
| 7,276,376 B2 | 10/2007 | Katayama et al. | |
| 2003/0068666 A1 * | 4/2003 | Zweig | 435/14 |
| 2005/0196820 A1 * | 9/2005 | Zweig | 435/14 |
| 2006/0110283 A1 | 5/2006 | Fish | |
| 2006/0124184 A1 * | 6/2006 | Ocvirk et al. | 137/833 |
| 2008/0064939 A1 * | 3/2008 | Reynolds et al. | 600/316 |
| 2008/0254446 A1 * | 10/2008 | Sode et al. | 435/6 |

FOREIGN PATENT DOCUMENTS

EP 2325636 5/2011

OTHER PUBLICATIONS

Garden, et al., "A Fluorescent Coagulation Assay for Thrombin Using a Fibre Optic Evanescent Wave Sensor", Biosensors and Bioelectronics 19 (2004) pp. 737-740.

Yang, et al., "Point-of-care Testing Portable Blood Coagulation Detectors Using Optical Sensors", Articles in Press, J. Med. Biol. Eng., May 28, 2012, doi: 10.5405/jmbe.1103.

* cited by examiner

*Primary Examiner* — Jill Warden
*Assistant Examiner* — Matthew Krcha
(74) *Attorney, Agent, or Firm* — Thomas | Horstemeyer, LLP

(57) ABSTRACT

In one embodiment, a device for measuring blood coagulation includes a substrate having a surface, an optical waveguide provided on the surface of the substrate, the waveguide having a tip, and means for spatially separating objects from the tip of the waveguide.

9 Claims, 3 Drawing Sheets

DEVICES AND METHODS FOR MEASURING BLOOD COAGULATION

CROSS-REFERENCE TO RELATED APPLICATION(S)

This application claims priority to U.S. Provisional Application Ser. No. 61/740,639, filed Dec. 21, 2012, which is hereby incorporated by reference herein in its entirety.

BACKGROUND

Measurement of the speed of blood coagulation is required for a large portion of the population. Malfunctioning of the coagulation system results in multiple disorders, from hemophilia and bleeding disorders (hemorrhage) to heart attacks and strokes related to unwanted clot formation (thrombosis). Anticoagulant medications are regularly taken by more than 2 million patients in the U.S. and are used during many surgical procedures to prevent blood from clotting in the presence of an open wound in the body.

There are several traditional approaches to the testing of blood coagulation. Two examples of such approaches are prothrombin time (PT) and thromboelastography (TEG). An estimated 800 million PT/INR assays are performed annually worldwide in the lab, together with the near-PT patient testing using CoaguChek. A PT test measures the time at which blood is declared "clotted" after the addition of reagents. The test is performed by moving a magnetic bead in a small amount of coagulating plasma. The moment at which the bead is unable to move is declared the point of coagulation. PT is a relatively inexpensive and fast test that can be performed on numerous samples in parallel. While these attributes are desirable, the test only works on blood plasma and only provides a single data point for the clotting process and therefore does not provide doctors any information about the dynamics of coagulation.

Unlike PT, TEG is capable of extracting additional information that can explain the reasons why something is wrong with the coagulation process. For example, TEG can be used to identify anomalies and show how clot strength is affected by hemophilia, thrombocytopenia, or abnormally strong clot formation. All this additional information is helpful for better diagnostics and monitoring of diseases. Because of this, TEG is considered the "gold standard" method. Unfortunately, the device used to perform TEG is very expensive (e.g., ~$35,000) and can only simultaneously run two samples with a testing time ranging from 10 to 30 minutes.

From the above discussion, it can be appreciated that it would be desirable to have an alternative way to continuously monitor blood coagulation that is low-cost, simple, sensitive, and capable of working with whole blood.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
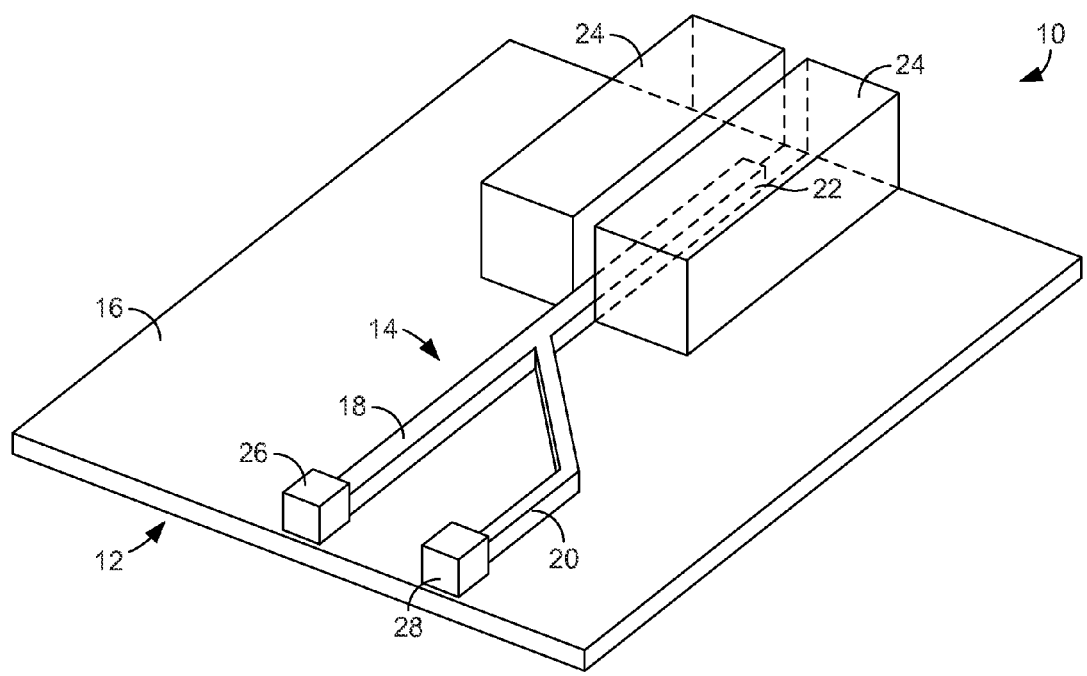
FIG. 1 is a top perspective view of an embodiment of a blood coagulation measurement device.

As expressed above, it would be desirable to have an alternative way to continuously monitor blood coagulation that is low-cost, simple, sensitive, and capable of working with whole blood. Disclosed herein are blood coagulation measurement devices that can facilitate such monitoring. In some embodiments, the device comprises a three-dimensional, on-chip photonic circuit that includes an optical waveguide that is used to measure the refractive index of the blood, which provides an indication of the degree of coagulation. Spacer elements are provided on the circuit to spatially separate red blood cells from the tip of the waveguide to eliminate or attenuate noise that could skew the coagulation measurement.

In the following disclosure, various specific embodiments are described. It is to be understood that those embodiments are example implementations of the disclosed inventions and that alternative embodiments are possible. All such embodiments are intended to fall within the scope of this disclosure.

As identified above, disclosed herein are devices that can be used to measure coagulation in blood. The designs are based on three-dimensional, on-chip photonic components serving two main purposes: (i) filtering out blood cells from whole blood, thus creating plasma, and (ii) continuously measuring the refractive index of that blood plasma. This enables the use of whole blood without centrifugation, thus solving a critical problem experienced by the blood testing community and opening up new approaches, such as in-vivo blood analysis, real-time coagulation monitoring, and others. Previously, optical measurements in blood were limited because of the presence of highly-scattering and absorptive blood cells, which interfere with many noise-sensitive optical setups and components. Because of this, samples were usually pre-processed, blood was centrifuged, and only plasma or serum was used for experiments. This limited tests to lab environments, introduced delays for sample processing, and required the drawing of relatively large volumes of blood even if the entire test could be performed using a single droplet.

With the disclosed devices, a drop of blood can be placed directly on the chip and all measurements can be conducted on blood plasma because of the three-dimensional filtering properties of the circuit. During coagulation, the refractive index of plasma increases. This refractive index can be measured to study the complex coagulation process. Notably, the on-chip photonic platform can be used in various other applications, including detection of hemolysis in whole blood, measurement of spectroscopic properties of plasma, and identification of multiple biomarkers of diseases near patients without the need for lab access. In addition, the principles described herein are applicable to other biomedical testing devices that analyze whole blood and other biological fluids. Furthermore, the devices can be easily packaged and integrated with mobile devices and laptops because no additional microfluidic components, such as channels, pumps, and controllers, are required in the disclosed approach.

The sensing is realized using continuous measurement of back reflection from an interface between an optical waveguide and separated blood plasma. In some embodiments, the waveguides can be surrounded by taller spacer elements of patterned material that physically separate the red blood cells from the waveguide tip. The drop of blood can be placed on top of the chip and will coagulate in a natural condition. No microfluidics components (pump, tubes, etc.) are required to operate the device. The surface of the device can be cleaned so that it is reusable or, alternatively, the device can be disposable since the mass production of such a chip has a low cost.

The refractive index of coagulating plasma can be measured using Fresnel's equation for reflectance, which is a related amount of power reflected from an interface between two media due to their refractive indices and light polarization. Although this is easy to measure in homogenous fluids, such as blood plasma, the presence of particles such as red blood cells makes coagulation measurement in whole blood difficult. In particular, the proximity of the red blood cells can create noise that would skew the refractive index calculation. It was for this reason that it was determined to isolate the sensing surface from the cells. In particular, it was determined to use spacer elements that provide for complete isolation of the waveguide tip from the cells.

FIGS. 1-4 illustrate an example embodiment of a blood coagulation measurement device 10, in the form of a three-dimensional on-chip photonic circuit, which incorporates the various design aspects discussed above. As is shown in these figures, the device 10 generally comprises a planar substrate 12 that supports an optical waveguide 14 that extends across a top surface 16 of the substrate. The substrate 12 is small in size as it only needs to accommodate a single drop of blood. In some embodiments, the substrate 12 has width and length dimensions in the range of approximately 100 to 1000 μm. The substrate 12 can be made of substantially any material that provided structural integrity to the device 10. Example materials include glass, plastic, silicon, or other rigid or flexible material. Regardless of the material used, at least the surface 16 has an index of refraction that is less than the index of refraction of the waveguide 14 so that any light that travels within the waveguide will be trapped by total internal reflection (TIR).

In the illustrated embodiment, the waveguide 14 comprises a linear primary branch 18 that extends across the top surface 16 of the substrate 12 in a direction parallel to a length direction of the substrate. In addition, the waveguide 14 comprises a secondary branch 20 that is coupled to the primary branch 18 and that extends across the top surface 16 of the substrate 12 in a direction diagonal to the length direction of the substrate and to the primary branch.

As shown in the figures, the waveguide 14 can have a generally rectangular (e.g., square) cross-section. The cross-sectional dimensions (e.g., height and width) of the waveguide 14 can, for example, be in the range of approximately 0.25 to 3 μm. Regardless of its size, the waveguide 14 is made of an optical material that transmits light well. In some embodiments, the waveguide 14 is made of a silicon material, such as polysilicon. One example construction for the device is a substrate 12 is made of silicon, a substrate surface 16 made of silicon dioxide, and a waveguide 14 made of polysilicon having an index of refraction that is higher than that of the silicon dioxide.

Provided along both sides of the primary branch 18 of the waveguide 14 at least at its distal end are spacer elements 24 that isolate at least the distal tip 22 of the waveguide. In particular, the spacer elements 24 ensure that red blood cells cannot get near the tip 22, in which case their proximity could skew the coagulation measurement. This is achieved by positioning the spacer elements so that the tip 22 of the waveguide 14 is located at a medial position along the lengths of the spacer elements 24. In the illustrated embodiment, the space elements 24 extend to the distal edge of the substrate 12 but the waveguide 14 terminates at a point inward from this edge. In the illustrated embodiment, the spacer members 24 each comprise a rectangular block of material that is formed on the top surface 16 of the substrate 12 in close proximity to the side edges of the primary branch 18 of the waveguide. In some embodiments, the spacer members 24 contact the side edges of the primary branch 18 and extend upward therefrom. In some embodiments, the spacer members 24 ensure that the cells cannot get any closer than approximately 20 to 25 μm to the tip 22 of the waveguide 14 from the horizontal (length) direction and approximately 2 to 3 μm from the top of the waveguide (i.e., the spacer members 24 are taller than the waveguide by at least 2 to 3 μm). The spacer members 24 can be made of substantially any material that has a lower index of refraction than the waveguide 14. In some embodiments, the spacer members 24 are made of sol-gel material, a polymer material, a glass material, or a dioxide silicon material.

Figure 2:
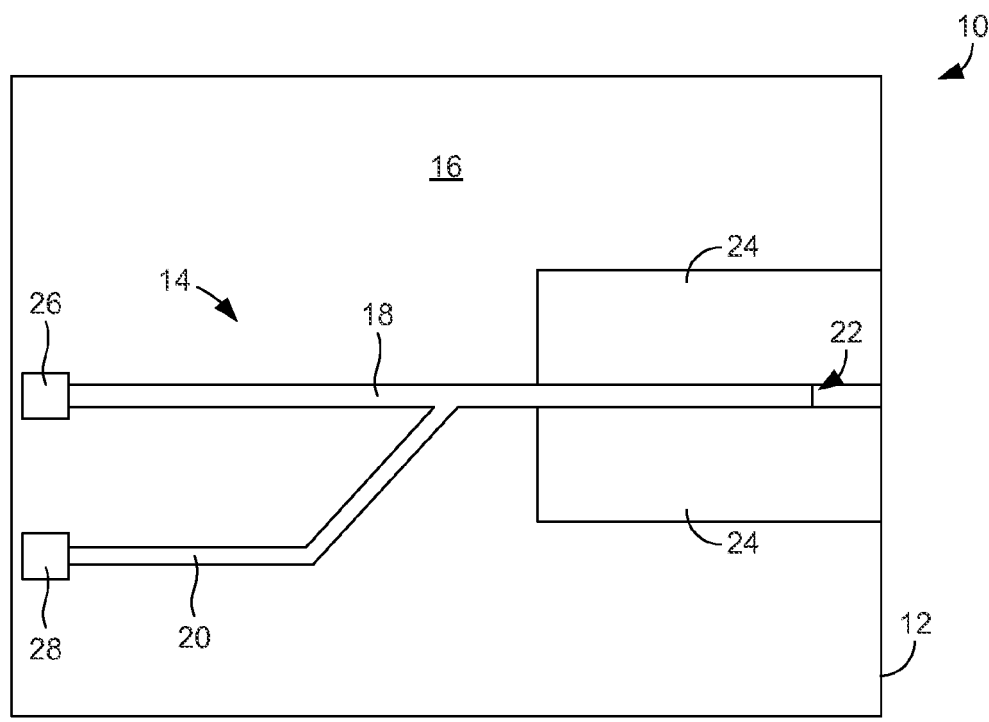
FIG. 2 is a top view of the device of FIG. 1.
Figure 3:
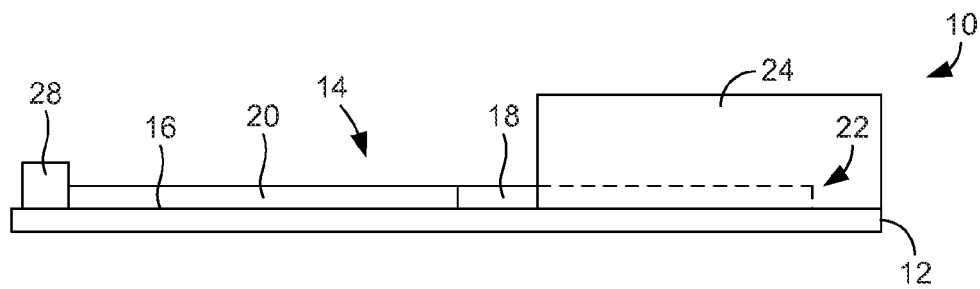
FIG. 3 is a side view of the device of FIG. 1.
Figure 4:
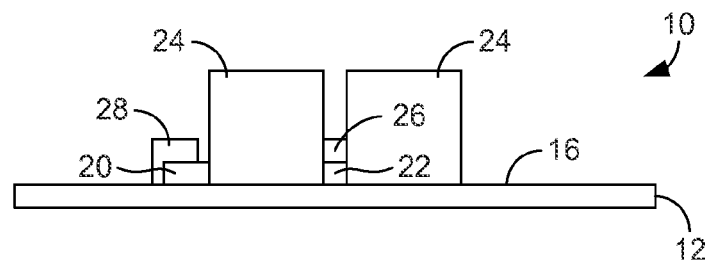
FIG. 4 is an end view of the device of FIG. 1.

With further reference to FIGS. 1 and 2, the device 10 can also include a light source 26 (e.g., laser source) that is coupled to the primary branch 18 of the waveguide 14. This light source 26 delivers light to the tip 22 of the waveguide 14, and therefore to the interface between the plasma and the waveguide. In addition, the device 10 can further include a light detector 28 that is coupled to the secondary branch 20 that receives light that is reflected back from the tip 22 of the waveguide 14. In other embodiments, however, both the light source and the light detector can be off-chip independent of the device 10. In such a case, light is received from and delivered to the off-chip independent components and reference numerals 26 and 28 can be thought of as representing optical couplers. It is further noted that, in some embodiments, a single waveguide could be used without secondary branching, and the light source and detector signals split performed by an off-chip splitter.

The device 10 shown in FIG. 1-4 can be fabricated using conventional chip fabrication techniques. One fabrication option is to create a self-aligned structure by first patterning thick sol-gel spacer elements and then depositing a thin layer of silicon to form a waveguide core.

Figure 5:
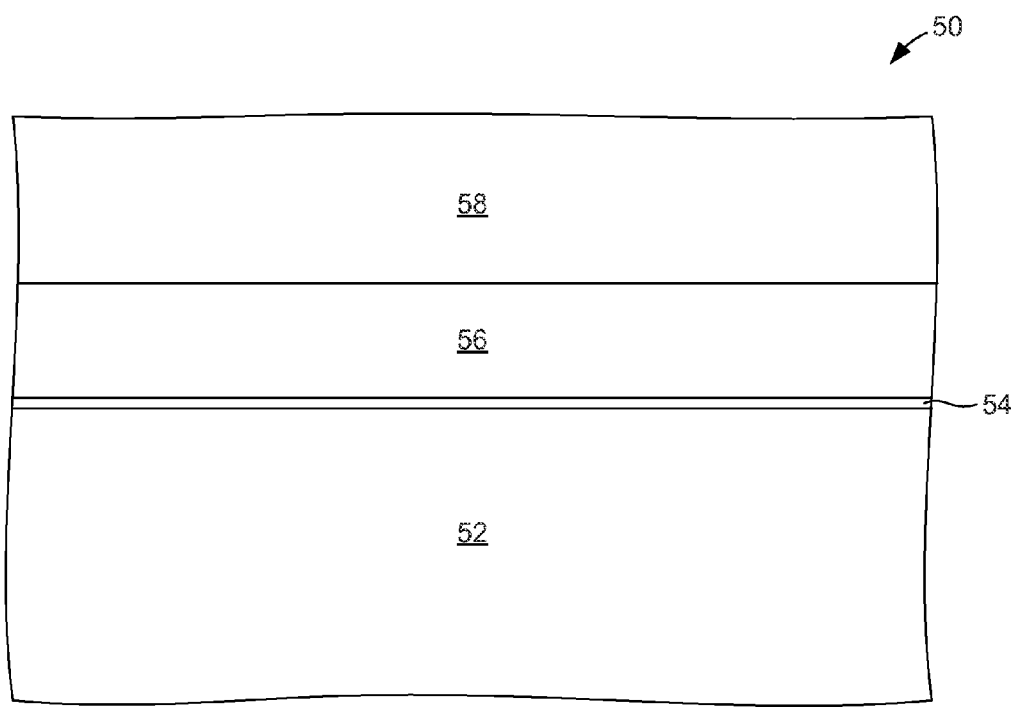
FIG. 5 is a schematic view of layers of an example blood coagulation measurement device.

FIG. 5 schematically illustrates various layers of an example blood coagulation measurement device 50, which can have a configuration similar to that shown in FIGS. 1-4. As shown in FIG. 5, the device 50 includes a silicon substrate 52 onto which has been deposited a silicon dioxide layer 54, which forms the top surface of the substrate. The substrate 52 can be approximately 50 to 1000 μm thick and the silicon dioxide layer 54 can be approximately 1 to 3 μm thick. Deposited on top of the silicon dioxide layer 54 is a polysilicon layer 56, which is used to form the waveguide of the device 50. The polysilicon layer 56 can be approximately 0.5 to 3 μm thick. Finally, a glass layer 58 is deposited on (e.g., spun on) the silicon dioxide layer 54, which is used to form the spacer elements of the device 50. The glass layer 58 can be approximately 5 to 10 μm thick.

The above-described devices can be used to measure blood coagulation. In such a case, a droplet of whole blood can be deposited on the device so as to cover the tip of its waveguide. Because of the presence of the spacer elements near the tip of the waveguide, red blood cells within the blood cannot get close to the tip. Accordingly, the presence of the red blood cells does not significantly affect the measurement and, in essence, the measurements will be based upon the blood plasma alone.

Light, for example having a wavelength of approximately 200 to 1600 nm, can be emitted by the light source and travel along the primary branch of the waveguide. Once the light reaches the tip of the waveguide, which is immersed in the blood plasma, it is reflected and travels backward along the primary branch of the waveguide. Some of this reflected light travels along the secondary branch (when provided) and is carried to the light detector. The light detected by the light detector can then be analyzed to determine aspects of the blood coagulation process, such as the speed of coagulation.

While the devices disclosed herein have been described as being adapted for measuring blood coagulation, it is noted that they could be used to measure other aspects of blood or other body fluids. Moreover, the devices could be used to measure properties of non-body fluids. For example, the devices could be used to test fresh water to determine how much or what type of particulate matter it contains.

The invention claimed is:

1. A method for measuring blood coagulation, the method comprising:
    placing a droplet of whole blood on a surface of a substrate of an on-chip photonic circuit including an optical waveguide so as to immerse a tip of the optical waveguide;
    spatially separating red blood cells within the whole blood from a the tip of the waveguide using spacer elements that are provided on the substrate surface so that only plasma of the whole blood contacts the waveguide tip;
    delivering light along the waveguide to the waveguide tip;
    sensing light that is reflected back from the tip of the waveguide; and
    determining a level of blood coagulation from the sensed light.

2. The method of claim 1, wherein the spacer elements comprise blocks of material deposited on the surface of the substrate that shield the tip of the optical waveguide.

3. The method of claim 1, wherein determining a level of blood coagulation comprises determining the refractive index of the plasma from the sensed light.

4. The method of claim 3, wherein determining a level of blood coagulation further comprises correlating the refractive index to a degree of coagulation of the blood.

5. The method of claim 1, wherein delivering light comprises emitting light from a light source provided on the on-chip photonic circuit into the optical waveguide.

6. The method of claim 1, wherein delivering light comprises delivering light having a wavelength of approximately 200 to 1600 nm.

7. The method of claim 1, wherein sensing light comprises sensing light using a light detector provided on the on-chip photonic circuit.

8. The method of claim 1, further comprising continuously delivering, sensing, and determining so as to continuously measure blood coagulation.

9. The method of claim 1, wherein the substrate has a lower index of refraction than the optical waveguide.

* * * * *